United States Patent [19]
Mozurkewich, Jr.

[11] Patent Number: 5,608,165
[45] Date of Patent: Mar. 4, 1997

[54] ULTRASONIC THICKNESS GAUGE FOR MULTILAYER PLASTIC FUEL TANKS

[75] Inventor: George Mozurkewich, Jr., Plymouth, Mich.

[73] Assignee: Ford Motor Company, Dearborn, Mich.

[21] Appl. No.: 642,988

[22] Filed: May 6, 1996

[51] Int. Cl.$^6$ ................................. G01N 29/20
[52] U.S. Cl. ............................... 73/599; 73/627
[58] Field of Search ............................ 73/599, 600, 602, 73/645, 659, 627, 629; 364/563

[56] References Cited

U.S. PATENT DOCUMENTS

| | | | |
|---|---|---|---|
| 3,538,751 | 11/1970 | Gericke | 73/616 |
| 3,748,895 | 7/1973 | Kummer et al. | 73/611 |
| 4,100,808 | 7/1978 | Evans et al. | 73/588 |
| 4,184,373 | 1/1980 | Evans et al. | 73/588 |
| 4,305,294 | 12/1981 | Vasile et al. | 73/579 |
| 4,394,824 | 7/1983 | Kanda et al. | 73/606 |
| 4,512,194 | 4/1985 | Beuter | 73/579 |
| 4,539,847 | 9/1985 | Paap | 73/579 |
| 4,570,486 | 2/1986 | Volkmann | 73/597 |
| 4,862,747 | 9/1989 | Boudy et al. | 73/631 |
| 4,875,372 | 10/1989 | Gilbert | 73/614 |
| 4,991,440 | 2/1991 | Pleinis et al. | 73/615 |
| 5,101,663 | 4/1992 | Narita et al. | 73/588 |
| 5,197,019 | 3/1993 | Delon-Martin et al. | 364/563 |
| 5,303,590 | 4/1994 | Modderman et al. | 73/588 |

OTHER PUBLICATIONS

Ultrasonic Testing, *Non–conventional testing techniques*, Edited by J. Szilard, Department of Electronic and Electrical Engineering University of Technology, Loughborough, UK, pp. 267–273 no date.

Methods of Experimental Physics: L. Marton and C. Marton, Editors–in–Chief, vol. 19, Ultrasonics, Academic Press, 1981, pp. 102–105, no month.

Measurement of the thickness of thin layers by ultrasonic interferometry, by M. Houze, B. Nongaillard, M. Gazalet, J.M. Rouvaen, and C. Bruneel, J. Appl. Phys., vol. 55, No. 1, Jan. 1984, pp. 194–198.

SAE Technical Paper Series, 900636, Development of Plastic Fuel Tank Using Modified Multi–Layer Blow Molding, by K. Fukuhara, M. Hara, N. Matsuura and H. Watanabe, Mazda Motor Corp., pp. 1–8, Feb. 26–Mar. 2, 1990.

SAE Technical Paper Series, 870304, Development of Mult–Layer Plastic Fuel Tanks for Nissan research Vehicle–II, by Y. Kurihara, K. Nakazawa, K. Ohashi, S. Momoo and K. Numazaki, Nissan Motor Co., Ltd., pp. 1–7, Feb. 23–27, 1987.

*Primary Examiner*—Christine K. Oda
*Attorney, Agent, or Firm*—Mark Mollon

[57] ABSTRACT

The thickness of a vapor barrier layer embedded in a co-extruded plastic fuel tank is measured using ultrasound. An interference method using ultrasonic tone-bursts employs a frequency progression wherein a frequency producing a minimum in the reflection echo from the barrier layer identifies the thickness of the barrier layer. The method is useful in polyethylene fuel tanks wherein an ultrasonic attenuation which is highly dependent upon frequency limits the resolution of barrier layer thickness.

8 Claims, 4 Drawing Sheets

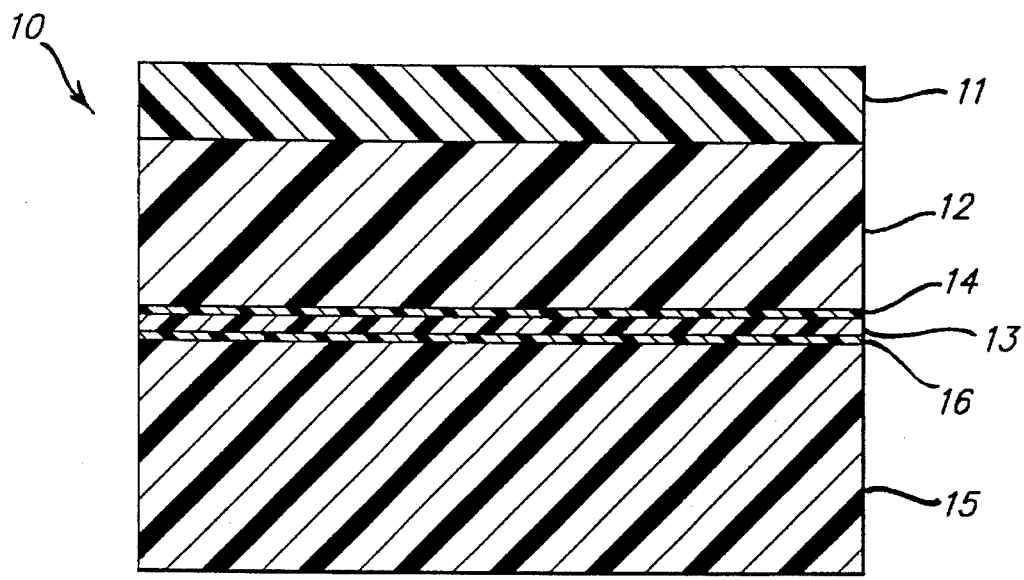
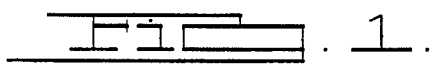
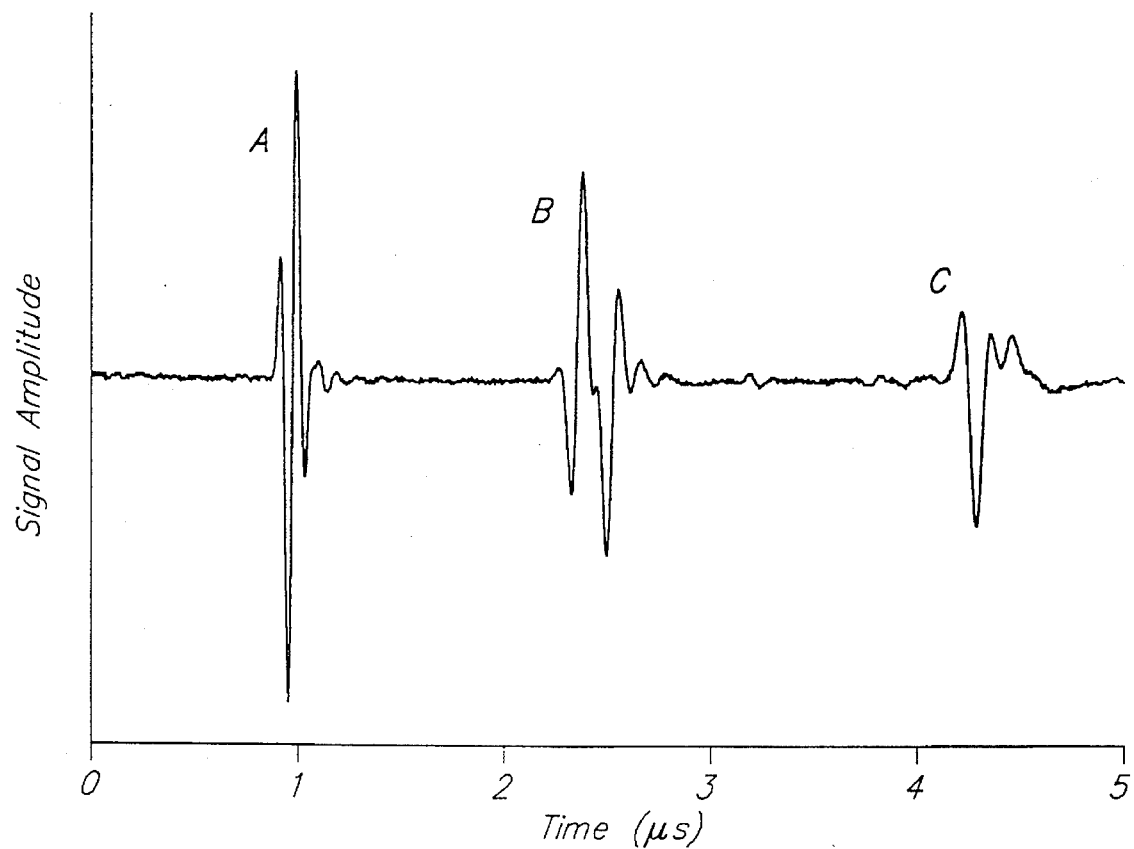
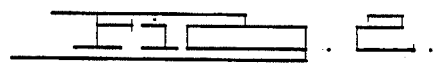

ULTRASONIC THICKNESS GAUGE FOR MULTILAYER PLASTIC FUEL TANKS

BACKGROUND OF THE INVENTION

The present invention relates in general to measuring the thickness of a thin layer in a multilayer structure using ultrasound, and more specifically to a tone-burst method for resolving an imbedded layer in a structure having high attenuation of ultrasonic pulses.

Polyethylene fuel tanks are used in automotive vehicles because of their light weight, durability, ease of molding into complex shapes, and corrosion resistance. Due to the high level of hydrocarbon permeation of polyethylene, however, hydrocarbon vapors could escape from a polyethylene fuel tank. Therefore, a barrier layer of a different polymer is normally incorporated into the tank wall by co-extrusion of the polyethylene and the barrier layer. The barrier layer is typically embedded between layers of polyethylene in order to provide structural protection of the barrier layer.

The thickness of various layers and, in particular, the presence and thickness of the barrier layer must be monitored during manufacture of the fuel tanks. Extrusion machines must be adjusted to provide proper thickness prior to a production run of tanks and then thickness must be monitored during production for purposes of quality assurance.

Destructive testing of sample tanks whereby a tank wall is cross sectioned and visually inspected to measure barrier layer thickness is undesirable due to the scrap created and the time required to conduct such a test. Therefore, a non-destructive and fast technique such as using ultrasound is preferred.

Conventional pulse-echo ultrasound is capable of measuring the thickness of outer and inner polyethylene layers as well as detecting the presence of a barrier layer. The conventional technique, however, is incapable of measuring the thickness of the barrier layer due to insufficient resolution.

SUMMARY OF THE INVENTION

The present invention has the advantage of accurate measurement of barrier layer thickness through a polyethylene layer without destructive testing of fuel tanks.

In one aspect, the invention provides a method of measuring thickness of a first layer made of a first material having first and second edges, the first edge contacting an adjacent layer made of a different material in a multilayer structure, the first layer having a thickness substantially less than the thickness of the adjacent layer. An ultrasonic pulse is transmitted into the structure through the adjacent layer toward the first layer. The ultrasonic pulse travels a first distance within the adjacent layer that is greater than the thickness of the first layer. The ultrasonic pulse has a duration less than the time required for the pulse to traverse the first distance and has a predetermined frequency. An echo-pulse corresponding to reflections from the first layer is received, the received echo-pulse including interference effects from within the first layer. A magnitude of the isolated echo-pulse is stored, and then the transmitting, receiving, and storing steps are repeated for a plurality of additional pulses while varying the predetermined frequency for each additional pulse according to a predetermined progression. The thickness of the first layer is determined in response to the frequency of a pulse that produced a minimum received echo-pulse magnitude.

BRIEF DESCRIPTION OF THE DRAWINGS

FIG. 1 is a cross-sectional view showing a multilayer plastic fuel tank structure.

FIG. 2 plots signal amplitude from a conventional pulse-echo ultrasonic interrogation of a multilayer fuel tank wall.

DETAILED DESCRIPTION OF PREFERRED EMBODIMENTS

Figure 3:
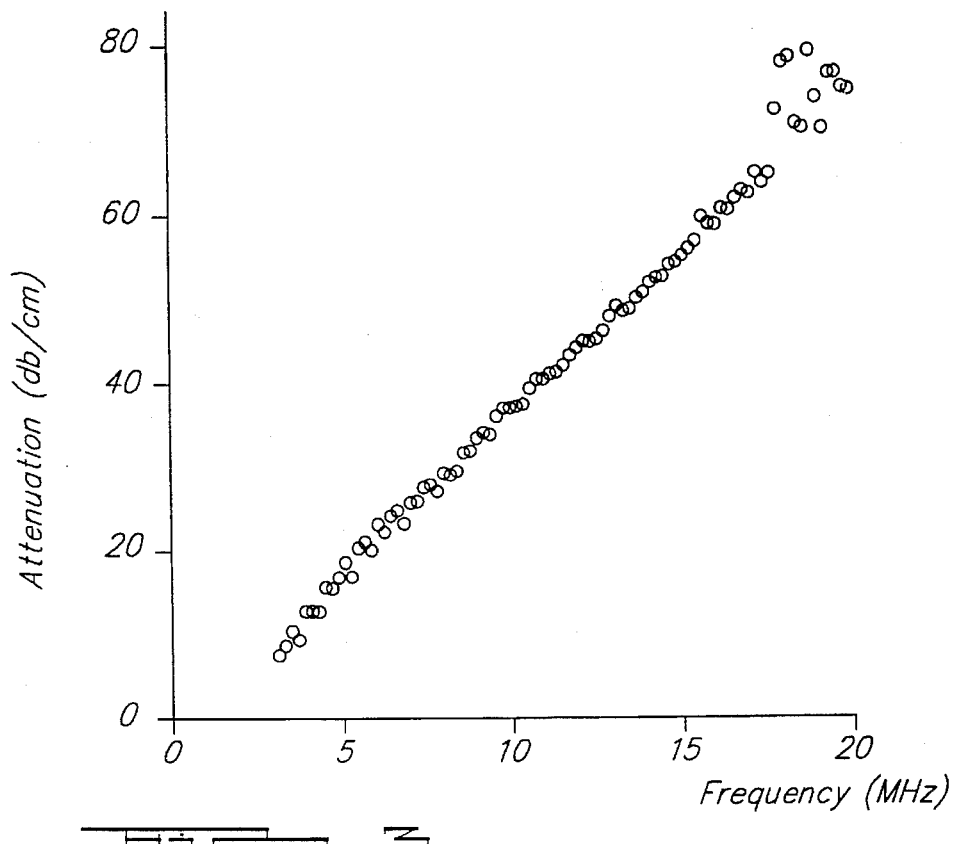
FIG. 3 plots ultrasonic attenuation in high-density polyethylene as a function of frequency.

FIG. 1 shows a cross-sectional view of a fuel tank wall 10 in a multilayer structure composed primarily of polyethylene. Tank wall 10 may be formed by co-extrusion of various layer materials as is known in the art. An exterior layer 11 of virgin high density polyethylene (HDPE) is mixed with carbon black which provides coloration. A second extruded layer 12 is comprised of virgin HDPE mixed with reground material obtained from flash (i.e., trimmings from manufacture fuel tank) and scrap to reduce waste from the manufacturing process. Layers 11 and 12 are almost identical in their composition and density so that together they appear as a single layer when making ultrasound measurements.

A vapor barrier layer 13 of ethylene vinyl alcohol (EVOH) co-polymer is joined to regrind layer 12 by a tie layer 14 consisting of low density polyethylene (LDPE) modified by mixing with a small amount of maleic anhydride which acts as an adhesive, i.e., it is able to stick to both layer 12 and layer 13. A tank interior layer 15 comprised of virgin HDPE is joined to barrier layer 13 by a second tie layer 16. Thus, barrier layer 13 has first and second edges defining a thickness which must be adequate to block hydrocarbon permeation.

A typical total thickness for a fuel tank wall ranges from about 2.5 to 9 mm and has a preferred thickness around 5 mm. With regard to thickness of each respective individual layer within wall 10, exterior layer 15 comprises about 15% of the total thickness, regrind layer 12 about 34%, each tie layer about 1.5%, barrier layer 13 about 3%, and interior layer 15 about 45%. Thus, the thickness of barrier layer 13 typically ranges from 66 to 270 μm.

Co-extrusion machinery used to manufacture polyethylene fuel tanks includes various settings for controlling the flow of material and thereby thickness of respective layers. Throughout a manufacturing run, the thickness of various layers must be monitored to assure product quality. For example, a minimum barrier layer thickness is required to prevent emission of fuel vapors in excess of acceptable limits. Conventional pulse-echo ultrasound techniques are sufficient to measure the thickness of the outer and inner polyethylene layers and to detect the presence of the barrier layer. Exterior layer 11 and regrind layer 12 are considered to be a single layer for purposes of ultrasound measurement since they are comprised of almost entirely the same material and no sufficient ultrasound reflection occurs at the edge between layers 11 and 12.

The use of conventional ultrasound in measuring the thickness of the barrier layer is impractical. As described below, the ultrasonic attenuation of HDPE is frequency selective, whereby higher frequencies are more greatly attenuated than lower frequencies. This prevents meaningful measurements of barrier layer thickness by pulse-echo techniques. This has necessitated destructive sectioning of the tank in order to optically measure the barrier layer thickness.

Conventional pulse-echo ultrasound uses the time of flight of sound pulses to determine thickness. A short pulse of ultrasound (i.e., an interrogation pulse) is introduced into a specimen and subsequent echoes from various embedded features are observed. The round-trip time interval $\Delta t$ between echoes is converted into spatial separation d between reflecting layers using the formula $$d = \frac{c\Delta t}{2}$$

where c is the speed of sound in the intervening material. For example, the speed of sound at 20° C. is about 2240 meters per second in HDPE and about 3330 meters per second in EVOH.

FIG. 2 shows a typical pulse-echo trace from a co-extruded fuel tank using ultrasound at 15 MHz. An echo A is received from the front surface of the tank wall, an echo B from the barrier layer, and an echo C from the back surface. Thus, the length of time between echoes A and B identify the thickness of the exterior HDPE layer, and the time between echoes B and C identify the thickness of the internal HDPE layer. No significant echoes are created at the interface between the tie layers and the polyethylene interior and exterior layers because of their similar composition and density. Within echo B are separate echoes from the first and second edges of the barrier layer, but they are not resolvable into separate echoes. Without two distinct reflections, conventional pulse-echo ultrasound is unable to determine layer thickness.

The resolution of conventional pulse echo ultrasound relates to the length of an interrogating pulse which can be no shorter than about one wavelength of the ultrasound frequency being used. The center frequency of pulse A in FIG. 2 equals about 12 MHz, corresponding to a layer thickness of between 130 and 140 µm that could theoretically be resolved. Nevertheless, a 200 µm layer is actually unresolved within echo B. The reason for this discrepancy in resolution is that the variability of ultrasonic attenuation according to frequency is quite substantial in polyethylene.

FIG. 3 shows measured attenuation of ultrasound in a 5 mm thick slab of HDPE. Attenuation is strongly dependent upon frequency, with higher frequencies suffering the most attenuation. The attenuation is comparable to lowpass filtering with a very sharp cutoff. Consequently, an input pulse centered at 15 MHz has its center frequency shifted to about 8 MHz after passing through a distance of 5 mm of polyethylene. The downshifted center frequency degrades resolution obtained using conventional pulse-echo measurements.

Figure 4:
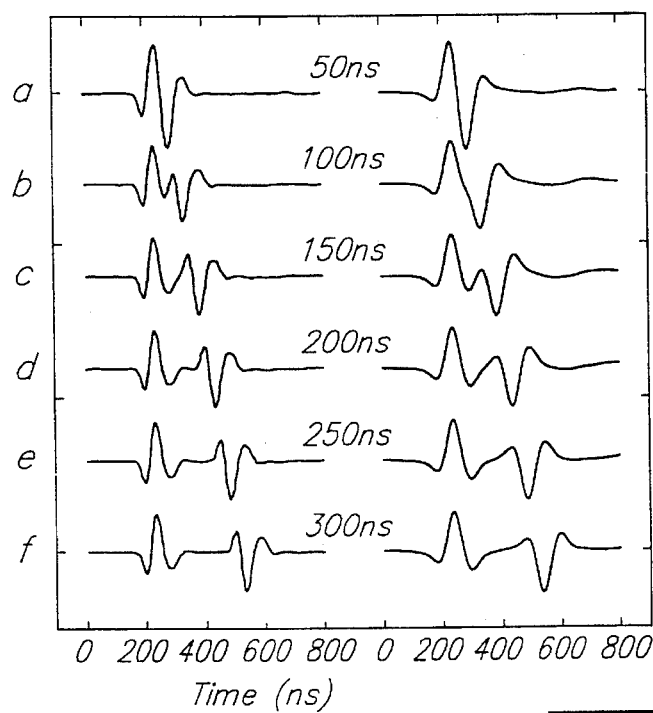
FIG. 4 plots simulated ultrasound echoes from an embedded barrier layer according to various layer thickness and shows the effects of attenuation in the intervening layer.

FIGS. 4a to 4f illustrate the effect of attenuation on the ability to resolve layers of various thicknesses. In FIG. 4a, a simulated pulse response is shown for an embedded layer having a thickness of 56 µm. The echo separation time $\Delta t$ of 50 ns between echoes from opposite edges of the barrier layer is unresolved in FIG. 4a, regardless of whether there is no significant attenuation (left-hand side of FIG. 4a) or significant attention from polyethylene (right-hand side of FIG. 4a). As shown in FIG. 4b, a 100 ns separation in echoes is just beginning to be resolved in the left-hand simulation without attenuation, but is still unresolvable in the presence of attenuation. At 150 ns in FIG. 4c, separate echoes are resolvable in the simulation without attenuation, but are only barely detectable in the simulation with attenuation. At a separation of 200 ns, separate echoes are clearly identified without attenuation but are only partially resolvable with attenuation. Separate echoes through an attenuating medium are more easily resolvable at 250 ns and 300 ns as shown in FIG. 4e and 4f, respectively. The attenuation echoes in FIG. 4 assume an outer HDPE layer with a thickness of 2.5 mm. Thus, the thinnest barrier layer of EVOH that can be resolved through a 2.5 mm thick layer of polyethylene corresponds to about 330 µm using 15 MHz ultrasound. It is not practical to attempt to measure thinner layers merely by increasing the ultrasound frequency because of the rapid increase of attenuation with frequency (i.e., frequency distortion) in polyethylene.

The present invention uses a tone-burst interference method to determined barrier layer thickness ultrasonically. When continuous-wave (CW) ultrasound is introduced into a layer of thickness d, the reflection from the front and back surfaces are phase-shifted relative to each other. In particular, if a layer made from one material is sandwiched or embedded between two layers of another material, then destructive interference will occur between the reflected ultrasound beams when the layer contains an integer number of half wavelengths of the ultrasound as shown in the following formula:

$$d = n\frac{\lambda}{2} = \frac{nc}{2f_n}$$

where $f_n$ is the frequency of the $n^{th}$ evenly spaced frequency of minimum reflectance.

The use of a "tone-burst" or a "gated sinewave" excitation causes continuous-wave interference within the thin barrier layer while preventing interference from echoes from other tank structures such as the front or rear tank surface. A tone-burst has a total duration T. If T is substantially longer than the reciprocal of the ultrasound excitation frequency, the resulting spectrum will be sufficiently narrow that the pulse frequency will be well defined even in the presence of strong attenuation. On the other hand, T must still be short enough that interference will occur only between the signals reflected from the front and back of the barrier layer. In other words, from the perspective of the barrier layer, the excitation lasts long enough to seem to be continuous wave, thereby allowing use of the interference method to determine thickness. From the perspective of the HDPE layers, the excitation is brief, thereby allowing time-of-flight echo determination of their thicknesses.

As shown in FIGS. 5a–5f, barrier layer thickness is determined by repeated ultrasound transmissions using transmission pulses which vary in frequency according to a predetermined progression, such as transmitting a pulse every 400 kHz from a starting frequency of 7.5 MHz to an ending frequency of 9.5 MHz. Of course, the size of the frequency steps depends upon the desired resolution.

FIGS. 5a–5f show reflected echo signals from a piece of multilayer fuel tank via an ultrasound probe and ultrasonic delay line for several different center frequencies. The first echo in each received signal is from the outside surface of the fuel tank, the second from the barrier layer, and the third from the inside surface. Thickness of the HDPE layers may be measured from the time intervals between echoes. The amplitude of the second echo in each received signal depends strongly on center frequency of the pulse since each is the superposition of reflections from each of the two edges of the barrier layer. The minimum reflection occurs in FIG. 5d, corresponding to a center frequency of 8.3 MHz. Using equation 2 above, the corresponding barrier layer thickness is 200 μm.

Figure 5:
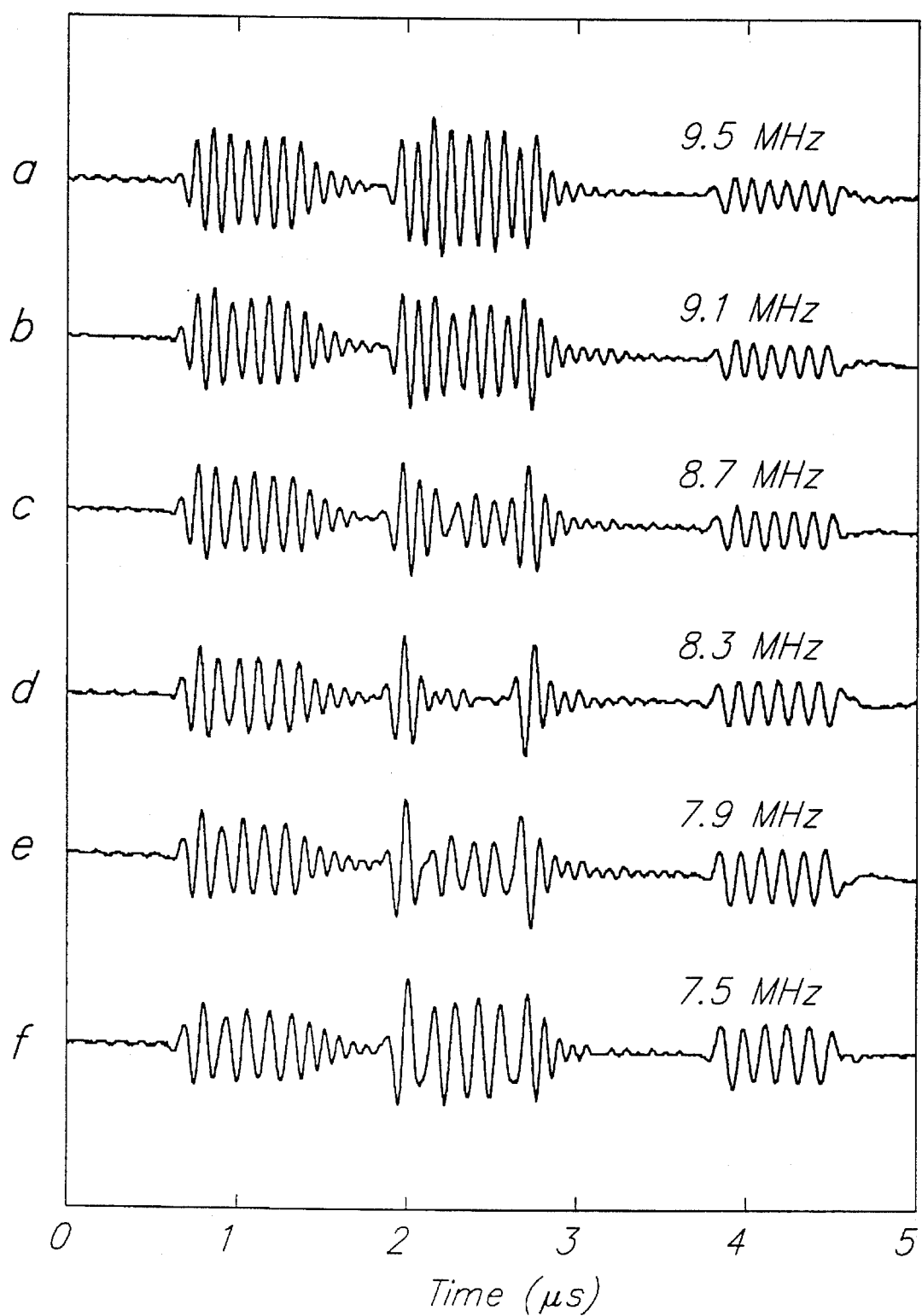
FIG. 5 plots tone-burst echoes from an embedded barrier layer for several different ultrasonic frequencies.

As shown in FIG. 5d, the echo pulse magnitude at the minimizing frequency includes two spikes at the initiation and completion of interference. These spikes can help a human operator to discriminate a minimum echo pulse and are useful in an automated apparatus to bracket the signal of interest.

Figure 6:
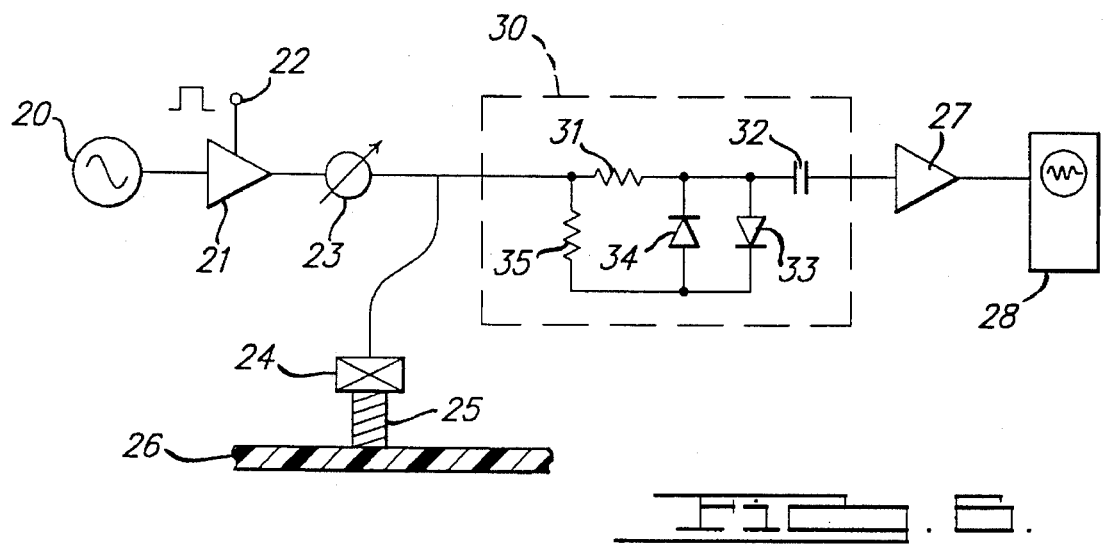
FIG. 6 is a block diagram showing one embodiment of apparatus for obtaining tone-burst measurements from a multilayer plastic fuel tank.

An apparatus for conducting ultrasonic measurements according to the present invention is shown in FIG. 6. A continuous-wave ultrasonic frequency voltage source 20 provides a selectable frequency output signal to the input of a gated power amplifier 21. CW source 20 is controllable to provide a desired ultrasonic frequency progression. A gate signal pulse having a duration T is provided to a gate input 22 of power amp 21 to produce ultrasonic pulses having a duration T. Gated ultrasonic signals are coupled through an attenuator 23 to an ultrasonic transducer 24. Attenuator 23 isolates Amp 21 from return echoes from transducer 24.

Transducer 24 converts an electric signal to an acoustic signal which is coupled through a delay line 25 into the wall of a fuel tank 26. Reflected ultrasonic signals return from fuel tank 26 through delay line 25 to transducer 24 which picks up the reflections and converts them to received echo signals that are coupled to a receiver amplifier 27. The amplified signals are displayed on an oscilloscope 28 to allow visual inspection of the ultrasound signals. A protection circuit 30 is connected between transducer 24 and the input of receiver amp 27 to protect the receiver amplifier from the large excitation voltage provided to transducer 24 from attenuator 23 (e.g., 70 volts peak may be required to provide sufficient ultrasound energy for an interrogation pulse). Protection circuit 30 includes a resistor 31 and a capacitor 32 connected in series between transducer 24 and receiver amplifier 27. A pair of crossed Schottky diodes 33 and 34 clamp the input of the receiver amplifier to an acceptably low voltage level. A resistor 35 is connected from the input of protection circuit 30 to ground.

The apparatus of FIG. 6 operates as follows. An ultrasonic pulse is transmitted into the fuel tank wall through the first outside polyethylene layer (e.g., layers 11 and 12 in FIG. 1) toward the barrier layer (e.g., layer 13 in FIG. 1). The ultrasonic pulse travels a first distance through the outside polyethylene layer that is greater than the thickness of the barrier layer. The ultrasonic pulse has a duration less than the time required for the pulse to traverse the first distance so that no interference occurs within the outside polyethylene layer. The ultrasonic pulse duration is controlled by gate pulse 22 applied to gated power amp 21 and may be derived from a monostable multivibrator, for example. The ultrasonic pulse has a predetermined frequency as determined by adjustment of CW source 20. A plurality of echoes are received after a predetermined delay following the transmission pulse. An echo-pulse corresponding to reflection from the barrier layer is isolated such that the isolated echo-pulse includes interference effects from within the barrier layer. The relative magnitude of the isolated echo-pulse is noted and/or stored for reference. The transmitting, isolating, and storing steps are repeated for a plurality of additional pulses while varying the predetermined frequency of each additional pulse according to a predetermined progression. In other words, the frequency provided from CW source 20 is adjusted to a new value and a new gate pulse is provided to gated power amp 21. Frequency adjustment and initiation of a gate pulse may be controlled either manual or automatically.

The thickness of the barrier layer is determined in response to the frequency of the pulse that produced the minimum isolated echo-pulse magnitude. Such minimizing frequency can be related to a thickness value either from a look-up table or by using the equation given above. However, since minima occur at integer multiples of the lowest minimizing frequency, a strategy should be employed to identify the lowest frequency producing a minimum. In one embodiment, a sufficiently low initial ultrasound frequency is selected which provides a half wavelength which is longer than the anticipated maximum thickness of the barrier layer (e.g., 5 MHz may be selected corresponding to a barrier layer thickness of 300 μm). Thereafter, frequency is increased in steps, with a step size depending upon the accuracy of measurement that is desired.

In an alternative embodiment, ultrasound pulses are provided using a frequency progression to identify two successive minima. The difference between two successive minima is approximately equal to the lowest minimum. In fact, the difference frequency may more accurately determine the layer thickness because of phase-shifting effects which impact the magnitudes of the frequency minima but which leave their spacing relatively unaffected.

Figure 7:
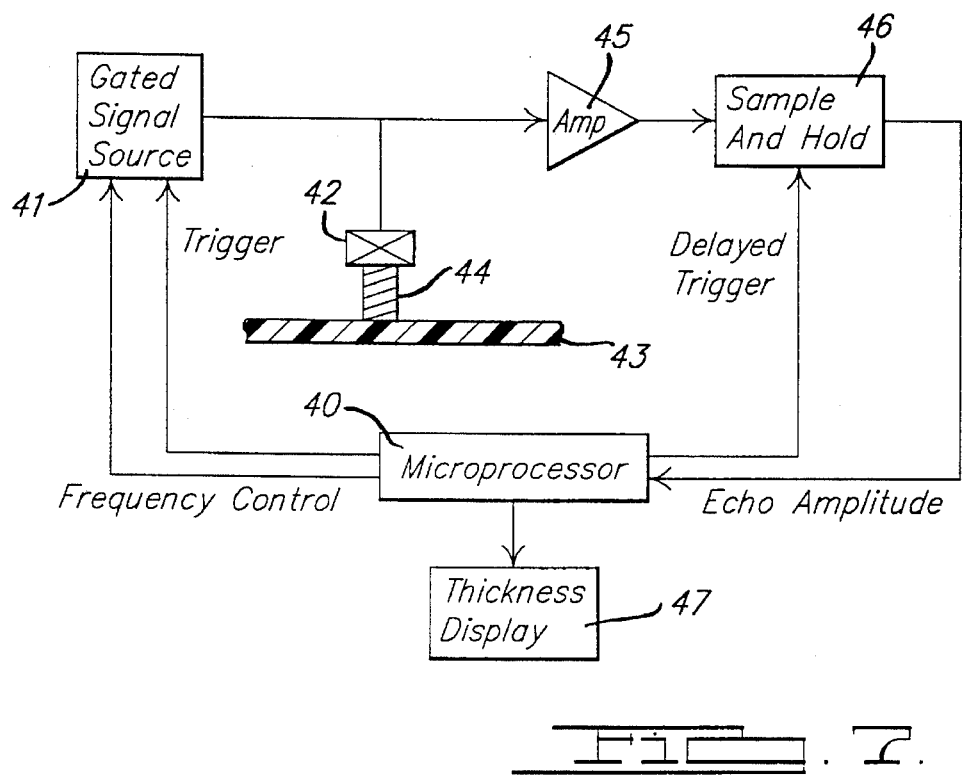
FIG. 7 is a block diagram showing an alternative embodiment of apparatus for obtaining ultrasonic tone-burst measurements.

FIG. 7 shows a preferred implementation of an automatic apparatus for determining thickness of both the barrier layer and the adjacent HDPE layers. A microprocessor 40 is programmed to coordinate a sequence of events for interrogating a fuel tank wall with ultrasound. A frequency control signal and a trigger signal are provided to a gated signal source 41 to selectively drive an ultrasonic transducer 42 coupled to a fuel tank wall 43 through an ultrasonic delay line 44 (composed of known delay line material such as polystyrene). A coupling gel is typically used at the interface between delay line 44 and fuel tank 43 to exclude air from the interface which would block passage of ultrasound. Ultrasound reflection echoes are picked up through transducer 42 and applied to the input of an amplifier 45. Amplifier 45 preferably includes a protection circuit similar to protection circuit 30 in FIG. 6. A sample and hold circuit 46 is connected to the output of amplifier 45 and is controlled by a delayed trigger signal from microprocessor 40. An echo amplitude from sample and hold circuit 46 is provided to microprocessor 40 which determines barrier layer thickness from a look up table or from calculation and the resulting thickness is displayed on a thickness display 47.

Microprocessor 40 coordinates the gated trigger signal to gated source signal 41 and the delayed trigger signal to sample and hold 46 according to the expected delay through the known delay line and the expected location of a barrier layer. Microprocessor 40 can optimize the trigger delay (i.e., a determination of the pulse locations) through an initial timing calibration using the sample and hold circuit.

The present invention can be adapted to measuring multiple embedded layers if each target layer's thickness is substantially less than that of the layers on either side of it. It can also be used to measure the thickness of a thin coating on the inaccessible side of a thicker layer. These measurements can be made even in media with high ultrasonic attenuation where the pulse-echo method is inadequate.

When measuring the thickness of an embedded layer between thicker layers where the two thicker layers are made of dissimilar materials having different acoustic impedances and where the acoustic impedance of the embedded layer has a value intermediate of those of the thicker layers, the formula using frequency minimum to relate to layer thickness is modified as follows:

$$d = \frac{n'c}{4f_n}$$

where n' is an odd integer (1, 3, 5, . . . ).

What is claimed is:

1. A method of measuring thickness of a first layer made of a first material having first and second edges, said first edge contacting an adjacent layer made of a different material in a multilayer structure, wherein said first layer has a thickness substantially less than a thickness of said adjacent layer, said method comprising the steps of:

transmitting an ultrasonic pulse into said structure through said adjacent layer toward said first layer, said ultrasonic pulse traveling a first distance within said adjacent layer that is greater than said thickness of said first layer, said ultrasonic pulse having a duration less than the time required for said pulse to traverse said first distance and having a predetermined frequency;

receiving an echo pulse corresponding to reflections from said first layer, said echo pulse including interference effects from within said first layer;

storing a magnitude of said echo pulse;

repeating said transmitting, receiving, and storing steps for a plurality of additional ultrasonic pulses while varying said predetermined frequency for each one of said additional ultrasonic pulses according to a predetermined progression; and determining said thickness of said first layer in response to the frequency of an ultrasonic pulse that produced a minimum echo pulse magnitude.

2. The method of claim 1 wherein said determining step includes finding the lowest frequency $f_0$ that provides said minimum echo pulse magnitude.

3. The method of claim 1 wherein said determining step includes finding a difference between two frequencies of said progression that provide respective minimum echo pulse magnitudes.

4. The method of claim 1 wherein said multilayer structure includes a second adjacent layer contacting said second edge of said first layer, thereby embedding said first layer between said adjacent layer and said second adjacent layer.

5. The method of claim 1 wherein said duration of each of said pulses is greater than the inverse of its predetermined frequency.

6. A method of measuring thickness of a barrier layer embedded in a plastic fuel tank, said barrier layer made of a first material impermeable to hydrocarbons and having first and second edges, said first and second edges contacting adjacent outer and inner layers, respectively, made of a polyethylene material in a multilayer tank wall, said method comprising the steps of:

transmitting an ultrasonic pulse into said tank wall through said outer layer toward said barrier layer, said ultrasonic pulse traveling a first distance within said outer layer that is substantially greater than said thickness of said barrier layer, said ultrasonic pulse having a duration less than the time required for said pulse to traverse said first distance and having a predetermined frequency;

receiving an echo pulse corresponding to reflections from said barrier layer, said echo pulse including interference effects from within said barrier layer;

storing a magnitude of said echo pulse;

repeating said transmitting, receiving, and storing steps for a plurality of additional ultrasonic pulses while varying said predetermined frequency for each one of said additional ultrasonic pulses; and determining said thickness of said barrier layer in response to the frequency of an ultrasonic pulse that produced a smallest echo pulse magnitude.

7. Ultrasonic apparatus for measuring thickness of a first layer made of a first material having first and second edges, said first edge contacting an adjacent layer made of a different material in a multilayer structure, wherein said first layer has a thickness substantially less than a thickness of said adjacent layer, and wherein said first layer thickness is measured using ultrasound passing through said adjacent layer, said apparatus comprising:

an ultrasonic transducer for transmitting vibrations to and receiving vibrations from said structure;

a signal source coupled to said ultrasonic transducer and producing a series of electrical transmission pulses causing said ultrasonic transducer to vibrate, each of said electrical transmission pulses having a respective frequency;

a receiver coupled to said ultrasonic transducer for receiving electrical echo signals produced in response to vibrations returning to said ultrasonic transducer from said structure after each respective electrical transmission pulse of said series of pulses, each of said electrical echo signals including a respective interference echo signal from said first layer; and a controller coupled to said signal source and said receiver, said controller controlling said signal source to cause each pulse of said series of pulses to have a pulse duration less than the time for a pulse to traverse through said structure to said first layer and to cause said series of pulses to provide a predetermined frequency progression, said controller selecting said interference echo signal resulting from each electrical transmission pulse from other electrical echo signals also resulting from each electrical transmission pulse, and said controller determining said thickness of said first layer in response to a respective frequency of said electrical transmission pulses that produces an interference echo signal having a minimum magnitude as compared to all other interference echo signals.

8. The apparatus of claim 7 further comprising an acoustic delay line for coupling between said ultrasonic transducer and said multilayer structure.

* * * * *